United States Patent [19]

Cummins

[11] Patent Number: 5,485,013
[45] Date of Patent: Jan. 16, 1996

[54] TURBIDITY SENSOR WITH A LIGHT APERTURE ARRANGEMENT OF TWO OPENINGS FORMED IN TWO PARALLEL PLATES

[75] Inventor: Brad L. Cummins, Freeport, Ill.

[73] Assignee: Honeywell Inc., Minneapolis, Minn.

[21] Appl. No.: 261,371

[22] Filed: Jun. 16, 1994

[51] Int. Cl.⁶ ........................................ G01N 15/06
[52] U.S. Cl. ............................. 250/574; 356/343
[58] Field of Search ....................... 250/574, 575; 356/339, 442, 343, 441, 340

[56] References Cited

U.S. PATENT DOCUMENTS

| | | |
|---|---|---|
| 3,114,253 | 12/1963 | Morey et al. . |
| 4,152,070 | 5/1979 | Kushner et al. ............... 250/574 |
| 4,160,914 | 7/1979 | Wynn ............................. 250/574 |
| 4,257,708 | 3/1981 | Fukuda ........................... 356/435 |
| 5,291,626 | 3/1994 | Molnar et al. ................. 356/339 |

FOREIGN PATENT DOCUMENTS

| | | |
|---|---|---|
| 0058576 | 8/1982 | European Pat. Off. . |
| 2485576 | 12/1981 | France . |
| 2068419 | 3/1982 | United Kingdom . |

OTHER PUBLICATIONS

Article titled "A New Control Device for Washing Machines Using a Microcomputer and Detectors", by Matsuo and Taniguchi, Sep. 1984, pp. 1171–1178.

*Primary Examiner*—Edward P. Westin
*Assistant Examiner*—Que T. Le
*Attorney, Agent, or Firm*—William D. Lanyi

[57] ABSTRACT

A turbidity sensor is provided with two plates which each have an aperture formed therethrough. The apertures are aligned to define a light passage from a light source such as a light emitting diode. By properly selecting the gap between the two plates and the size of the two apertures, the angle of divergence light emanating from the light source can be controlled and reduced to a magnitude that prevents light from passing directly from the light source to a scattered light detector of the turbidity sensor. The arrangement avoids the necessity of using expensive focusing lenses.

17 Claims, 7 Drawing Sheets

TURBIDITY SENSOR WITH A LIGHT APERTURE ARRANGEMENT OF TWO OPENINGS FORMED IN TWO PARALLEL PLATES

BACKGROUND OF THE INVENTION

Field of the Invention

The present invention is generally related to an aperture for use in association with a detector system and, more particularly, for use in conjunction with a light source of a turbidity sensor.

Description of the Prior Art

Turbidity sensors are well known to those skilled in the art. They are intended to detect the amount of particulate matter within a fluid stream. Both turbidimeters and nephelometers incorporate a light source and one or more light sensitive elements. In certain types of turbidity meters, a light emitting diode is arranged to transmit a beam of light directly toward a first light sensor. A second light sensor can be positioned to receive light which is scattered by particulate matter in the fluid stream. In one particular type of turbidity sensor, the first light sensor receives a diminishing amount of light as a result of increased turbidity and the second light sensor receives an increasing amount of light as a result of increased turbidity. A ratio of the signals from the two light sensors can be used as an indication of the turbidity of the flowing medium.

U.S. Pat. No. 5,331,177, which issued to Kubisiak et al on Jul. 19, 1994, discloses a turbidity sensor that is provided with a light source and a plurality of light sensitive components which are disposed proximate a conduit to measure the light intensity directly through the conduit from the light source and at an angle therefrom. The direct light beam and scattered light beam are compared to form a relationship that is indicative of the turbidity of the liquid passing through the conduit. The rate of change of turbidity is provided as a monitored variable.

U.S. patent application Ser. No. 08/246,895 which was filed on May 20, 1994 by Foreman et al and assigned to the assignee of the present application, describes a plurality of fluid condition sensors that are combined together to provide a sensor cluster that senses turbidity, temperature, conductivity and the movement of the ferromagnetic object. The plurality of sensors are attached to a substrate and encapsulated, by an overmolding process, with a light transmissive and fluid impermeable material. The sensor cluster can be disposed at numerous different locations within a body of fluid and does not require a conduit to direct the fluid to a particular location proximate the sensor. A circuit is provided which monitors the signal strength of first and second light sensitive components that are used to determine turbidity and, in addition, those signal strengths are also used to advantageously determine the most efficient magnitude of current necessary to drive a light source, such as a light emitting diode. By controlling the current to a light emitting diode as a function of the strength of light signal received by first and second light sensitive components, the turbidity sensor can be operated more efficiently and effectively.

U.S. patent application Ser. No. 08/246,902 which was filed on May 20, 1994 by Boyer et al, discloses a plurality of fluid condition sensors that are combined together to provide a sensor cluster. The sensor cluster avoids the use of a tubular channel as normally provided in turbidity sensors. The cluster is particularly adapted for use in a pump housing to take advantage of the relative lack of bubbles and foam in the bottom portion of the pump housing. By providing a plurality of sensors as part of a single cluster, costs can be reduced and the cluster enables a plurality of sensors to be located in a common region.

U.S. Pat. No. 5,291,626, which issued to Molnar et al on Mar. 8, 1994, describes a machine for cleansing articles which incorporates a device for measuring the turbidity of a partially transparent liquid. The machine can be a dishwasher or clothes washer and the device includes a sensor for detecting scattered electromagnetic radiation and a sensor for detecting transmitted electromagnetic radiation.

French Patent Number 2,485,576, which was issued to Hazan et al and published on Dec. 31, 1981, describes a washing machine that uses a light source and two light receiving elements. One of the light receiving elements provides a signal that is used during washing cycles and the other light receiving element is used during rinsing cycles. The signals represent the degree of turbidity of the washing fluid and are monitored periodically to detect the change in turbidity of the fluid during the respective washing and rinsing cycles.

A problem that occurs in turbidity sensors is the unintentional receipt of light by the scattered light detector directly from the light source. If the beam of light emanating from the light source diverges by a sufficient amount, it can fall on the scattered light detector and cause it to provide a signal even when no particulate matter is contained within the flowing medium. To prevent this divergence of the light beam, a laser can be used. In addition, certain turbidity meters employ focusing lenses to prevent the divergence of light from the light source directly toward the scattered light detector. If focusing lenses are not used, an aperture can be formed in a plate which is placed in front of the light source. However, as will be described in greater detail below, light can be reflected from the inner surfaces of the aperture and can be directed in a disadvantageous direction toward the scattered light detector. It would therefore be significantly advantageous if a light source could be provided with an inexpensive aperture that prevents the reflected divergence of the light beam while avoiding the expense that is inherent in the use of focusing lenses.

SUMMARY OF THE INVENTION

A turbidity meter made in accordance with the present invention comprises a light source and a light detector disposed at a first location to receive light from the light source along a first line. A first plate, with a first aperture formed therethrough, is disposed in association with a second plate which has a second aperture formed therethrough. The first and second plates are spaced apart from each other. The first and second apertures are aligned with each other to define a light passage along the first line through the first and second plates. The light source is disposed on a first side of the light passage and the light detector is disposed on a second side with the first and second plates being disposed between the light source and the light detector. In a particularly preferred embodiment of the present invention, a second light detector is disposed to receive light along a second line which is disposed at a preselected angle to the first line. In a typical application of the present invention, the preselected angle is approximately 90 degrees. The first and second plates are spaced apart by a first dimension and the light source is spaced apart from a most proximate one of the first and second plates by a second dimension. The first and second dimensions define an angle of divergence of the light in association with the light passage.

In a preferred embodiment of the present invention, the light source is a light emitting diode and the first and second light detectors are photodiodes. However, it should be understood that other light sensitive components can be used in conjunction with the present invention and other light sources can also be used to provide the source of light. In addition, it should be understood that a single light sensor could be used. The arrangement of the present invention can be a portion of a turbidity sensor.

BRIEF DESCRIPTION OF THE DRAWINGS

The present invention will be more fully understood from a reading of the Description of the Preferred Embodiment in conjunction with the drawings, in which.

DESCRIPTION OF THE PREFERRED EMBODIMENT

Figure 1:
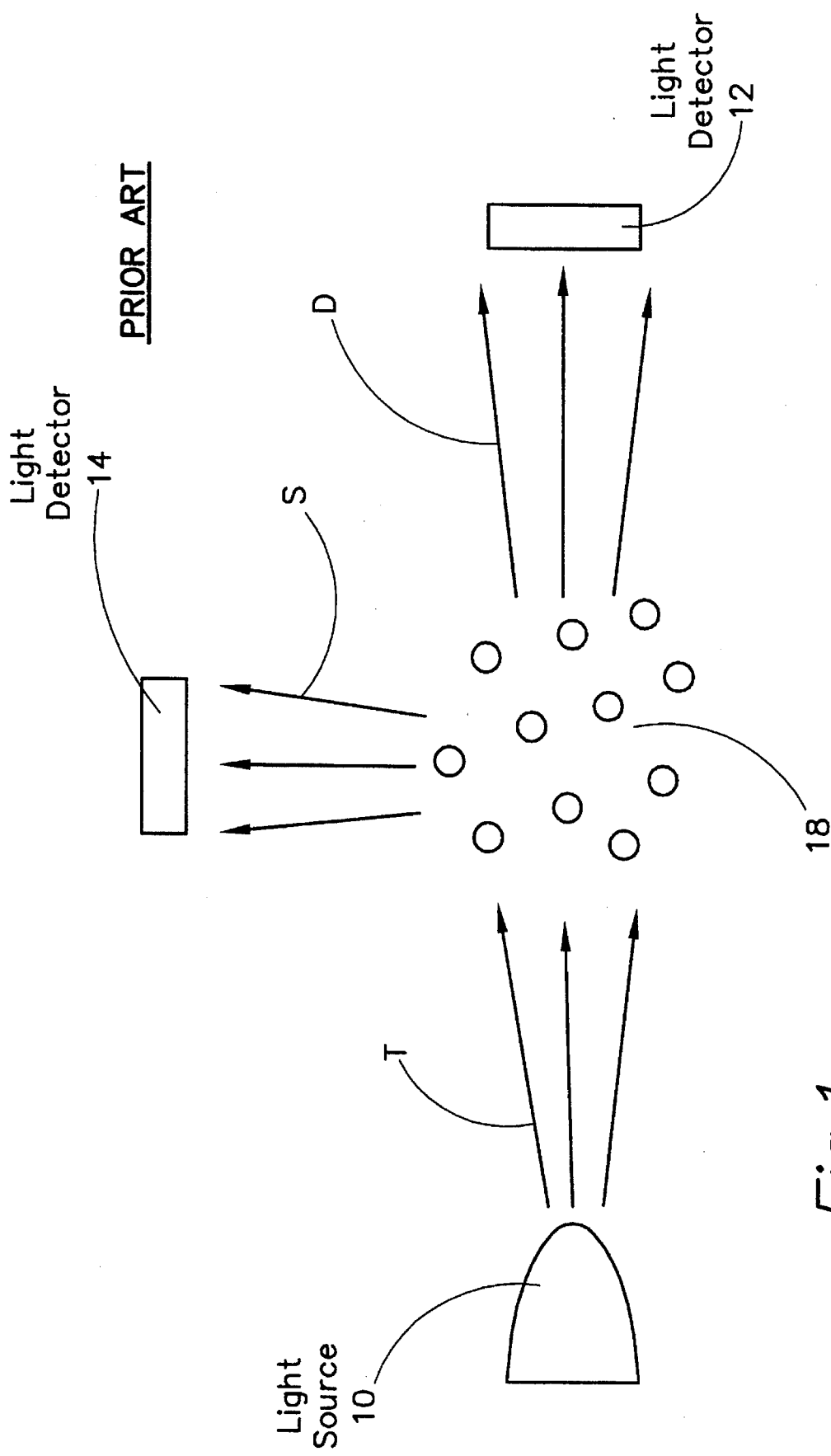
FIG. 1 illustrates a schematic arrangement of a light source, a first light detector and a second light detector.

Throughout the Description of the Preferred Embodiment of the present invention, like components will be identified by like reference numerals.

FIG. 1 illustrates a typical arrangement of a light source and two light detectors in a turbidity sensor. The light source 10 can be a light emitting diode and the two light detectors, 12 and 14, can be photodiodes or photoresistors. The first light detector 12 is placed in a location to receive light directly from the light source 10 and the second light detector 14 is placed at a location to receive light in a direction that is generally 90 degrees from the line between the light source 10 and the first light detector 12.

Light which is emitted by the light source 10 travels in a diverging path represented by arrows T. Some of that light travels directly through the medium, such as water, toward the first light detector 12 as represented by arrows D. A portion of the transmitted light T is diffused by particulates 18 and travels in a scattered path represented by arrows S toward the second light detector 14. The first and second light detectors, 12 and 14, each provide a signal representing the magnitude of light received. As the amount of particular matter 18 increases, the direct light D decreases and the signal provided by the first light detector 12 also decreases. As the particulate matter 18 increases, the scattered light S increases along with the signal provided by the second light detector 14. The signals received by the second light detector 14 and the first light detector 12 can be combined as a ratio to represent the degree of turbidity in the flowing medium. Although the present invention is described as having two light detectors, it should be understood that it could be operated with a single scattered light detector 14.

Figure 2:
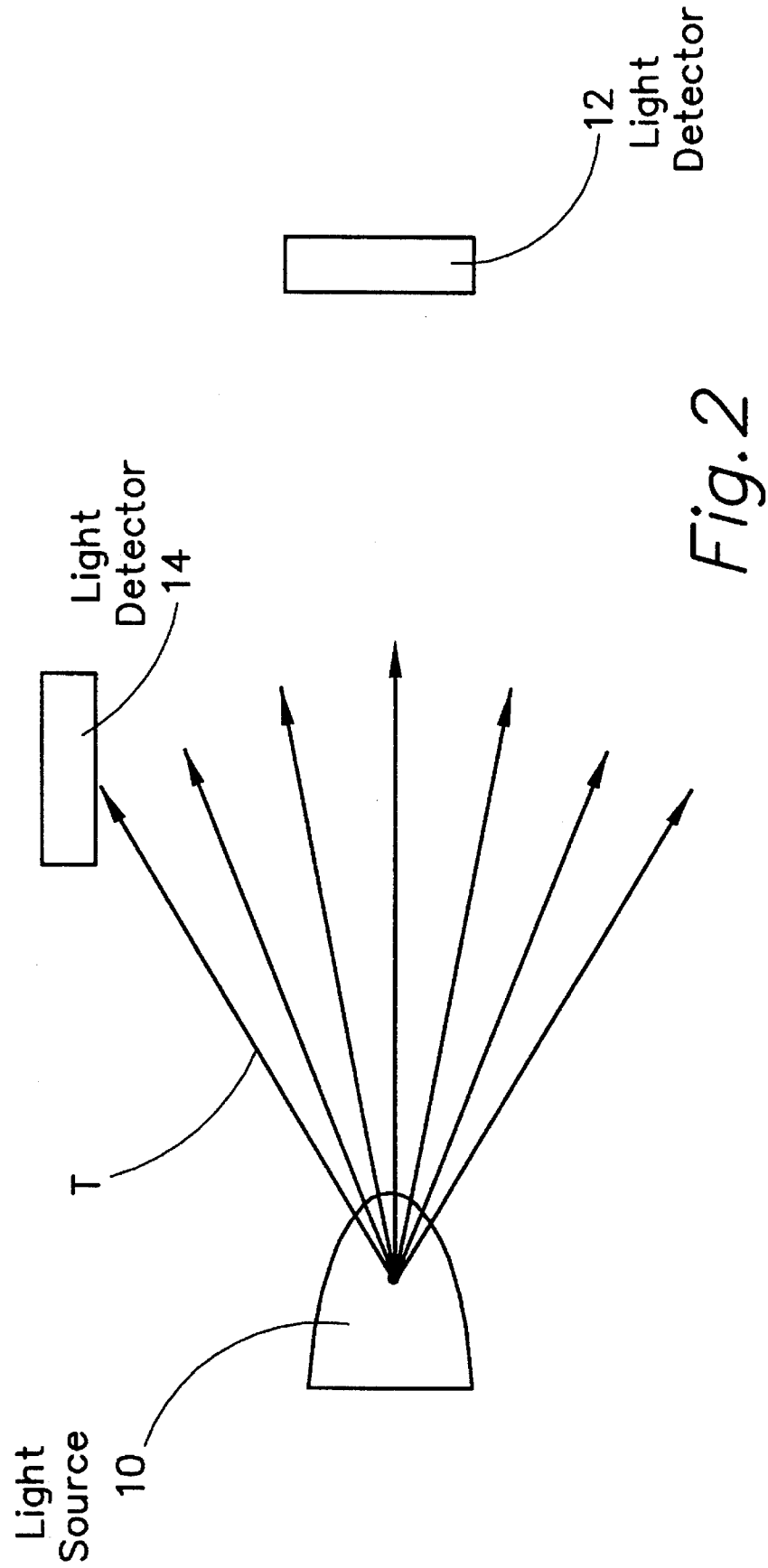
FIG. 2 schematically illustrates a problem that can occur when a light source is arranged in conjunction with first and second light detectors.

FIG. 2 shows a schematic representation that illustrates a problem that can occur in known turbidity sensors. The divergent light T transmitted from the light source 10 can diverge at an angle that is sufficient to cause light to flow directly from the light source 10 to the second light detector 14. Therefore, even when no particulate matter 18 is present in the flowing medium, a signal will be provided by the second light detector 12. Obviously, this direct passage of light from the light source 10 to the second light detector 14 will adversely affect the accuracy of a turbidity sensor.

Figure 3:
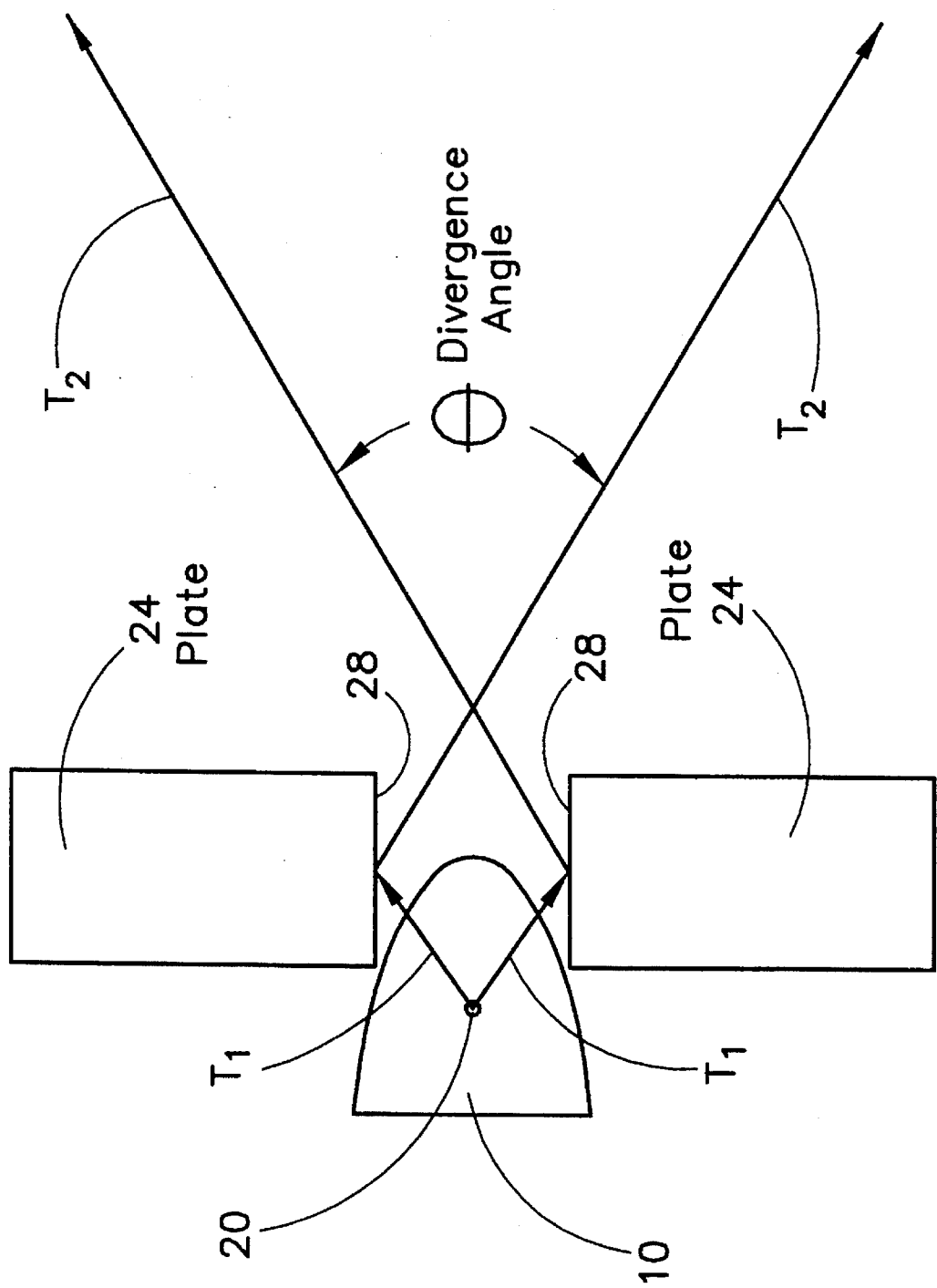
FIG. 3 is a geometric arrangement of a light source and a plate which has the disadvantage of permitting reflected light to pass from the light source to a scattered light detector without being diffused by particulate matter.

FIG. 3 illustrates one possible way of providing an aperture for a system such as that shown in FIG. 1. For purposes of this discussion, the light emanating from the light source 10 will be presumed to originate at a point 20. In a light emitting diode, this point source of light is essentially the manner in which light is generated. A plate 24 can be provided with an aperture as shown. The aperture is aligned with the light source 10 to minimize the divergence of light as illustrated as in FIG. 2. However, the surfaces of the aperture which are identified by reference numeral 28 can reflect light. If the light emanates from point 20, as indicated by arrows $T_1$, it can be reflected from surface 28 in the directions represented by arrows $T_2$. Unless the width of plate 24 is extreme, the angle of divergence 8 can be significant and, in certain applications, could result in the deleterious condition illustrated in FIG. 2. This is particularly true if the light source 10 is placed close to the plate 24. Obviously, if the light source 10 is moved toward the left in FIG. 3 and spaced apart from the plate 24 by a significant distance, the magnitude of angle 8 can be decreased, but this type of arrangement would disadvantageously increase the size of the sensor and reduce the light intensity.

Figure 4:
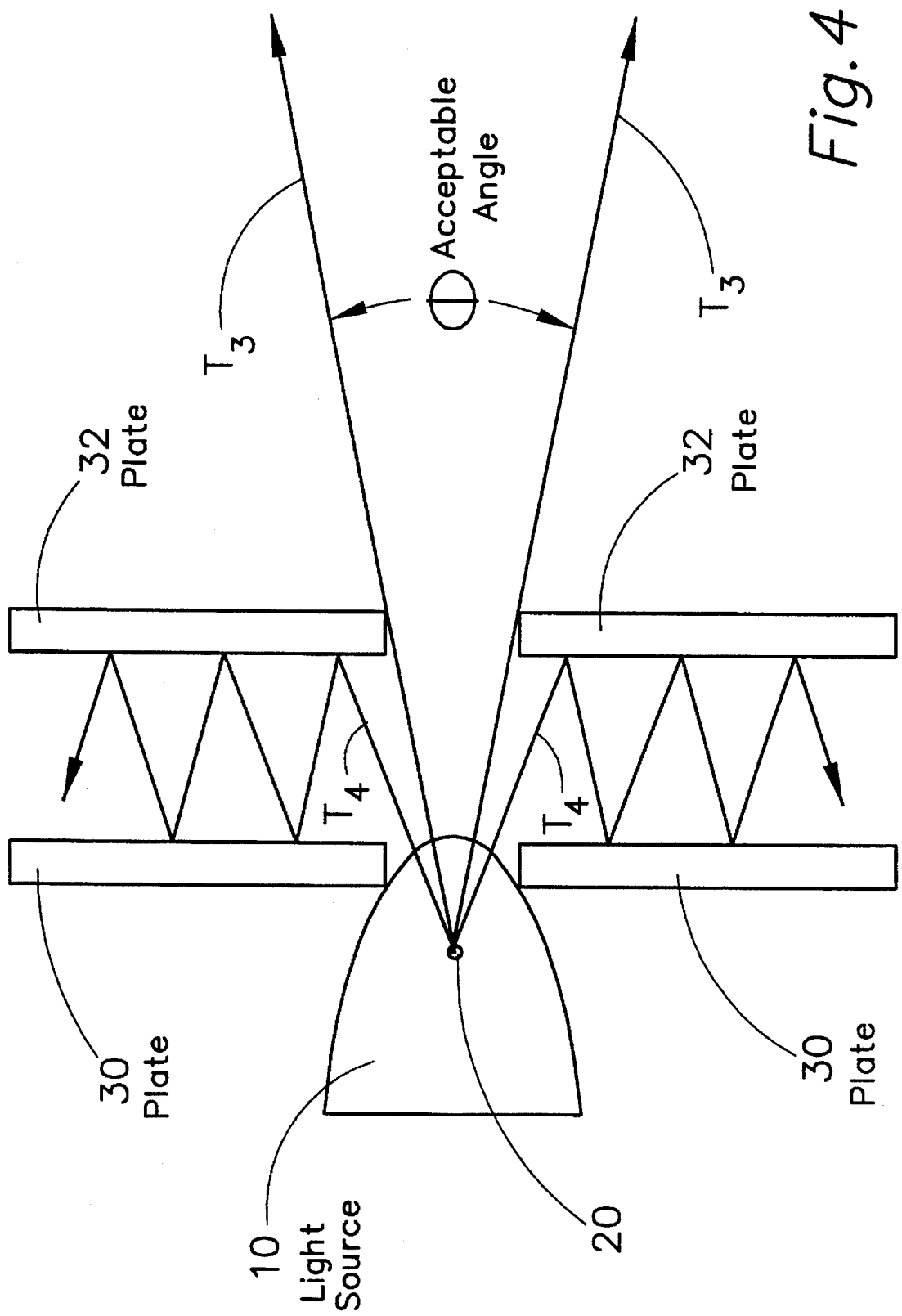
FIG. 4 is a schematic representation of the first and second plates of the present invention arranged in conjunction with a light source to show how the present invention prevents light from passing from the light source along a divergent path greater than a preselected angle.

FIG. 4 is a schematic illustration of the present invention. It comprises a first plate 30 and a second plate 32. Each of the two plates is provided with an aperture formed through it. The apertures are aligned along a line extending from the point 20 toward an intended target, such as the first light detector 12 shown in FIG. 1. Some of the light, represented by arrows $T_3$, passes along the light passage formed by the two apertures. This light has an angle of divergence Φ. Other light emanating from the point 20, at an angle which is greater than the acceptable angle Φ, passes from point 20 but does not pass completely through the light passage formed by the two apertures. This light is identified by arrows $T_4$. Rather than reflecting from the surfaces of the apertures, as described above in conjunction with FIG. 3, the light is reflected along the space between the first and second plates and is dissipated without being permitted to enter the region where the first and second light detectors are located. The configuration shown in FIG. 4 illustrates how the divergent light which passes from point 20 in directions outside the range identified by angle , is prevented from passing into the area where the fluid flows between the light source 10 and the region where the first and second light detectors, 12 and 14, are located.

Figure 5:
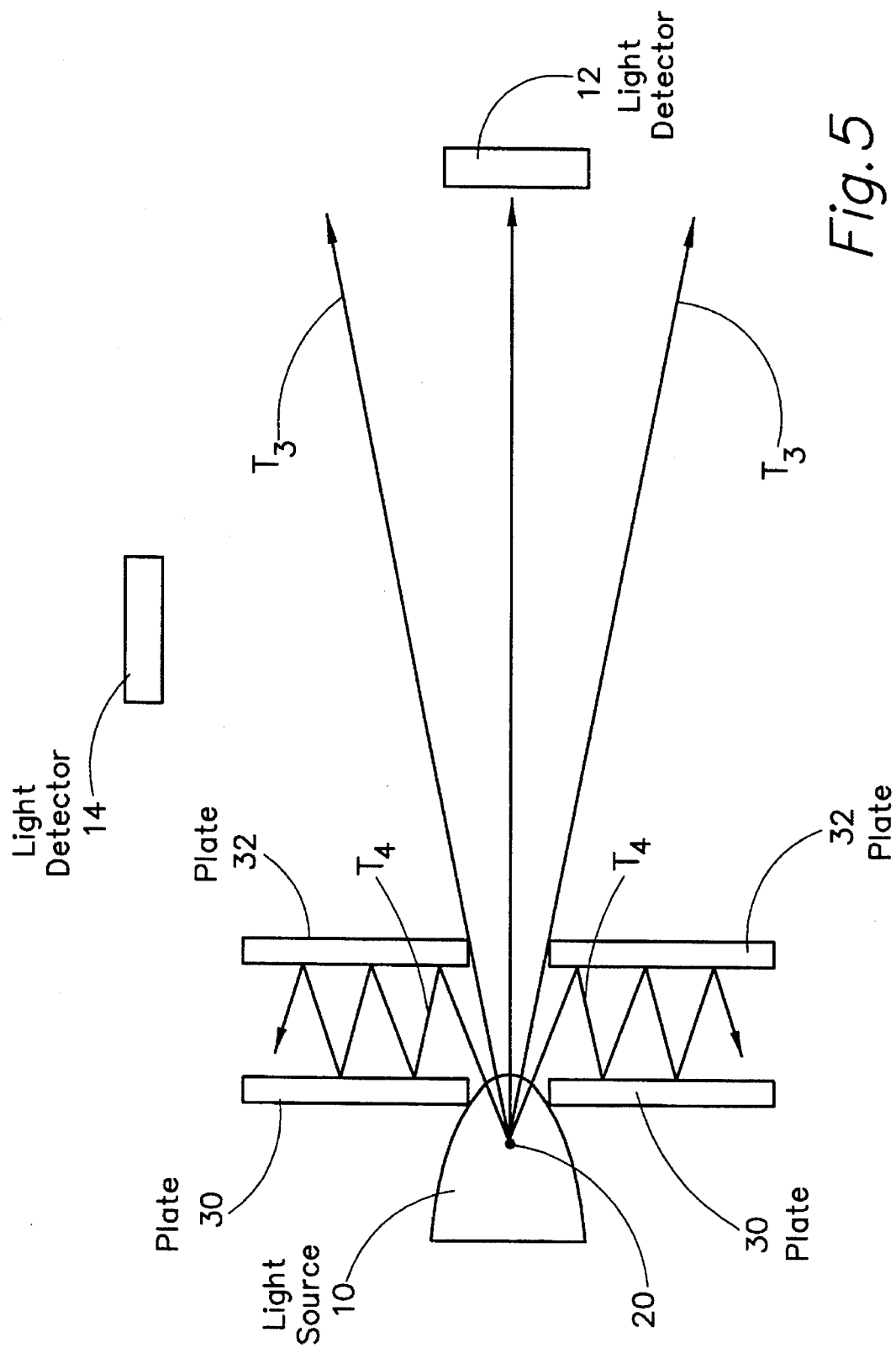
FIG. 5 shows a representation of FIG. 4 in combination with first and second light detectors.

FIG. 5 shows the illustration of FIG. 4 in combination with the locations of the first and second light detectors, 12 and 14. It illustrates how the light passage formed by the apertures in plates 30 and 32 prevent light from passing directly from point 20 to the second light detector 12 as described above in conjunction with FIG. 2. The light that would otherwise pass directly from point 20 toward the second light detector 14 is trapped in the space between the first and second plates, 30 and 32, and prevented from entering the region between the light source 10 and the light detectors. Most importantly, the light is prevented from passing directly from point 20 to the second light detector 14.

Figure 6:
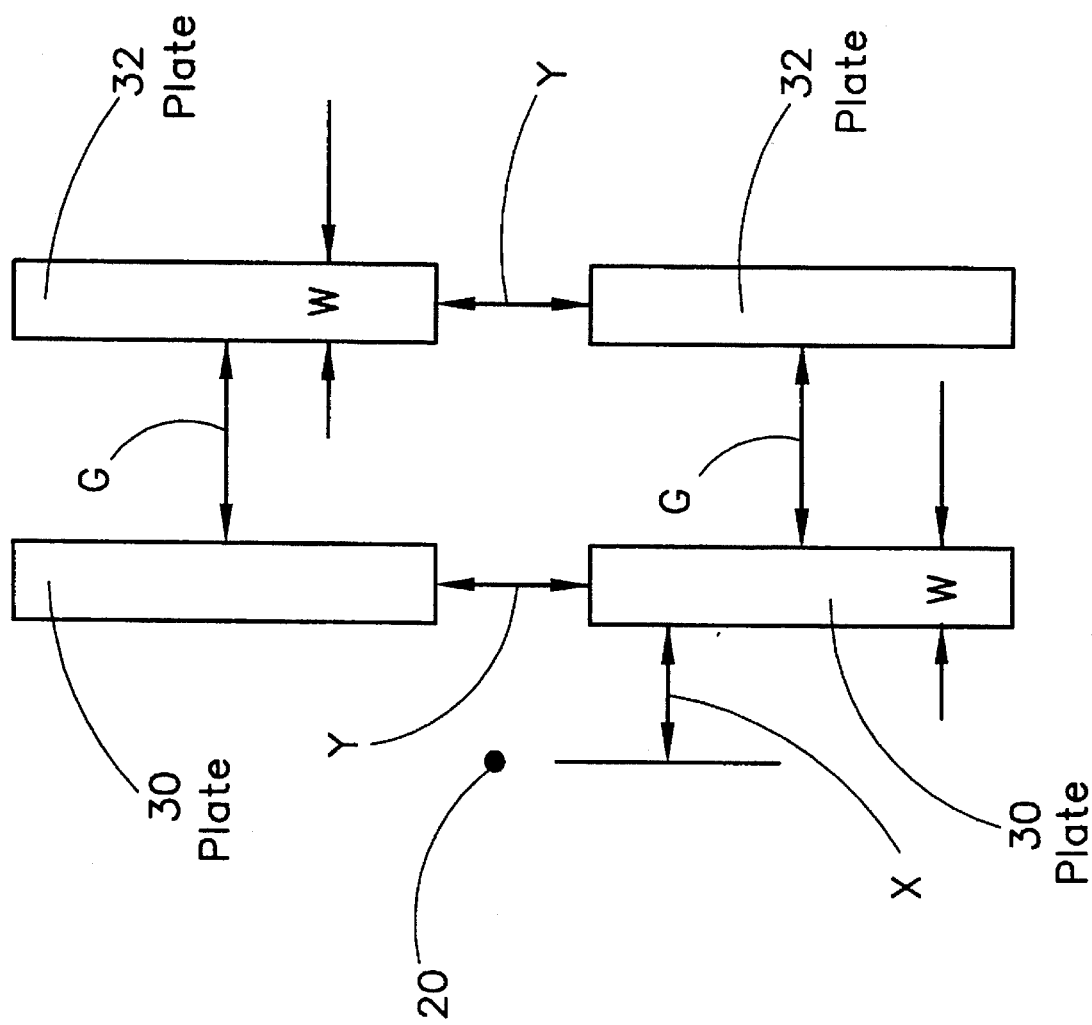
FIG. 6 shows the relevant dimensions of the components of the present invention.

For purposes of the following description of the present invention, FIG. 6 shows the relative dimensions of the components used to form the light passage between point 20 and the first light detector 12. The first and second plates, 30 and 32, are provided with apertures that have a diameter identified by reference letter Y. Although a preferred embodiment of the present invention uses apertures in the first and second plates which are generally identical to each other, it should be clearly understood that this identity of dimension Y is not necessary in all embodiments of the present invention. Through the use of simple geometry, the magnitude of angle which will be described in greater detail below can be calculated as a function of the sizes of two differently shaped apertures in the first and second plates. However, for purposes of this description, identically shaped and sized apertures will be used. The widths of the first and second plates are identified by reference letter W. Similarly, it should be understood that although the first and second plates are illustrated as having identical widths, this is not necessary in all embodiments of the present invention. The first and second plates, 30 and 32, are spaced apart by a gap identified by arrow G. The point source 20 is spaced apart from the first plate 30 by the distance represented by arrow X.

With continued reference to FIG. 6, it should be understood that the plates can have different thicknesses W and differently sized apertures Y. In addition, the distance between point 20 and the first plate 30 can be changed to suit each particular application of the present invention.

Figure 7:
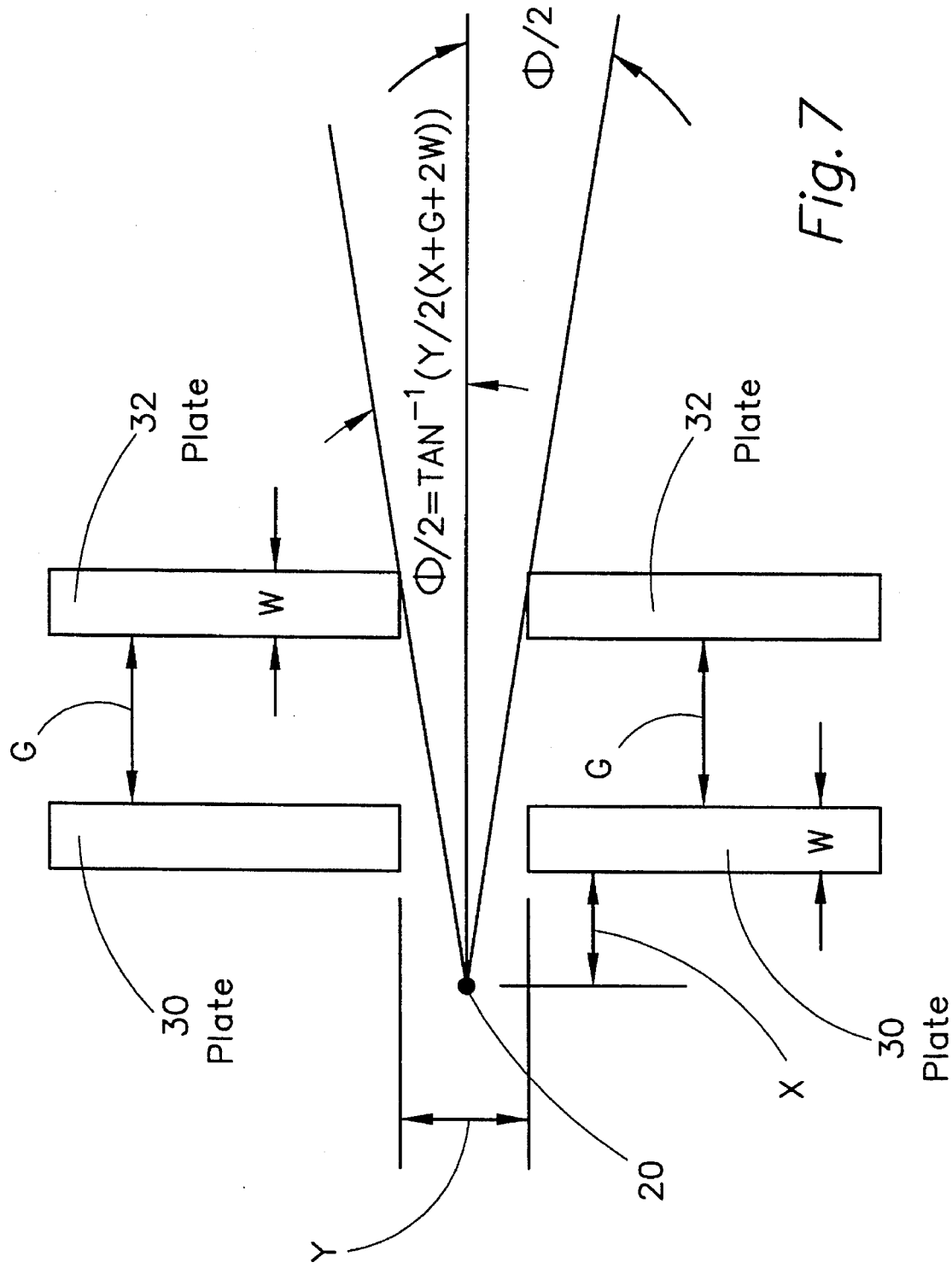
FIG. 7 shows the mathematical relationship between the components of the present invention and a divergent beam emanating from a light source.

FIG. 7 shows the relationship between the dimensions described above in conjunction with FIG. 6 and the angle of divergence Φ. As illustrated in FIG. 7, the angle of divergence Φ is equal to twice the arc tangent of dimension Y divided by twice the sum of dimension X plus dimension G plus two times dimension W. This is represented in equation 1 below.

$$\Phi = 2\mathrm{TAN}^{-1}(Y/2(X+G+2W))$$

With reference to FIG. 7 and equation 1, it can be seen that the angle of divergence Φ can be decreased by increasing dimension X or dimension G. In addition, it can be seen that the angle of divergence Φ will be increased in response to an increase in dimension Y or a decrease in dimension W.

Through the use of the concepts of the present invention, the angle of divergence of a light beam emanating from a light source can be significantly reduced without the need for focusing lens which would otherwise increase the cost of a turbidity sensor. In addition, the use of two plates with apertures formed therethrough prevents light from being reflected from the surfaces of the apertures in the deleterious way described above in conjunction with FIG. 3. By appropriately locating the first and second plates with respect to the light source, the angle of divergence can be reduced to prevent the passage of light directly from the light source to the second light detector 14. This prevents the second light detector 14 from receiving light other than that which is diffused by particulate matter. As a result, the accuracy of a turbidity sensor can be significantly improved without increasing the costs of the device.

The embodiments of the invention in which an exclusive property or right is claimed are defined as follows:

1. A light detector arrangement, comprising:

a light source;

a first light detector disposed at a first location to receive light from said light source scattered along a second line at a preselected angle to a first line;

a first plate having a first aperture formed therethrough; and a second plate having a second aperture formed therethrough, said first and second plates being spaced apart from each other, said first and second apertures being aligned to define a light passage along said first line through said first and second plates through which a divergent and unfocused beam of light can pass from said light source, said first light source being disposed on a first side of said light passage, said light detector being disposed on a second side of said light passage with said first and second plates being disposed between said first light source and said light detector, said first and second plates preventing said divergent and unfocused beam of light from passing directly from said light source to said first light detector, said first and second plates being spaced part by a first dimension, said light source being spaced part from a most proximate one of said first and second plates by a second dimension, said first and second dimensions defining an angle of divergence of said light in association with said light passage.

2. The arrangement of claim 1, further comprising:

a second light detector disposed to receive light directly along said first line.

3. The arrangement of claim 2, wherein:

said second line is generally perpendicular to said first line.

4. The arrangement of claim 1, wherein:

said light source is a light emitting diode.

5. The arrangement of claim 1, wherein:

said first light detector is a photodiode.

6. The arrangement of claim 2, wherein:

said second light detector is a photodiode.

7. The arrangement of claim 1, wherein:

said arrangement is a portion of a turbidity sensor.

8. A light detector arrangement, comprising:

a light source;

a first light detector disposed at a first location to receive light from said light source along a first line;

a first plate having a first aperture formed therethrough;

a second plate having a second aperture formed therethrough, said first and second plates being spaced apart from each other, said first and second apertures being aligned to define a light passage along said first line through said first and second plates through which a divergent and unfocused beam of light can pass from said light source, said light source being disposed on a first side of said light passage, said light detector being disposed on a second side of said light passage with said first and second plates being disposed between said light source and said light detector; and a second light detector disposed to receive light along a second line which is disposed at a preselected angle to said first line, said first and second plates preventing said divergent and unfocused beam of light from passing directly from said light source to said first light detector, said first and second plates being spaced apart by a first dimension, said light source being spaced apart from a most proximate one of said first and second plates by a second dimension, said first and second dimensions defining an angle of divergence of said light in association with said light passage.

9. The arrangement of claim 8, wherein:

said second line is generally perpendicular to said first line.

10. The arrangement of claim 8, wherein:

said light source is a light emitting diode.

11. The arrangement of claim 10, wherein:

said first light detector is a photodiode.

12. The arrangement of claim 11, wherein:

said second light detector is a photodiode.

13. The arrangement of claim 12, wherein:

said arrangement is a portion of a turbidity sensor.

14. A light detector arrangement, comprising:

a light source;

a first light detector disposed at a first location to receive light from said light source along a first line;

a first plate having a first aperture formed therethrough;

a second plate having a second aperture formed therethrough, said first and second plates being spaced apart from each other, said first and second apertures being aligned to define a light passage along said first line through said first and second plates through which a divergent and unfocused beam of light can pass from said light source, said light source being disposed on a first side of said light passage, said light detector being disposed on a second side of said light passage with said first and second plates being disposed between said light source and said light detector; and a second light detector disposed to receive light along a second line which is disposed at a preselected angle to said first line, said arrangement being disposed within a turbidity sensor, said first and second plates preventing said divergent and unfocused beam of light from passing directly from said light source to said first light detector, said first and second plates being spaced apart by a first dimension, said light source being spaced apart from a most proximate one of said first and second plates by a second dimension, said first and second dimensions defining an angle of divergence of said light in association with said light passage.

15. The arrangement of claim 1, wherein:

said second line is generally perpendicular to said first line.

16. The arrangement of claim 15, wherein:

said light source is a light emitting diode.

17. The arrangement of claim 16, wherein:

said first light detector is a photodiode; and said second light detector is a photodiode.

\* \* \* \* \*